United States Patent
Wong et al.

(10) Patent No.: US 6,703,389 B2
(45) Date of Patent: *Mar. 9, 2004

(54) METHOD OF TREATING CHRONIC PAIN

(75) Inventors: Erik H. F. Wong, Portage, MI (US); Saeeduddin Ahmed, Indianapolis, IN (US); Robert C. Marshall, Mattawan, MI (US); Robert McArthur, Kalamazoo, MI (US); Duncan P. Taylor, Kalamazoo, MI (US); Lars Birgerson, Martinsville, NJ (US); Pasquale Cetera, Annandale, NJ (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/020,261

(22) Filed: Dec. 14, 2001

(65) Prior Publication Data

US 2002/0061910 A1 May 23, 2002

Related U.S. Application Data

(62) Division of application No. 09/599,213, filed on Jun. 22, 2000, now Pat. No. 6,465,458.
(60) Provisional application No. 60/141,968, filed on Jul. 1, 1999, provisional application No. 60/144,131, filed on Jul. 16, 1999, provisional application No. 60/158,256, filed on Oct. 6, 1999, and provisional application No. 60/170,381, filed on Dec. 13, 1999.

(51) Int. Cl.$^7$ .............................................. A61K 31/535
(52) U.S. Cl. .................... 514/239.2; 514/238.5
(58) Field of Search ..................... 514/239.2

(56) References Cited

U.S. PATENT DOCUMENTS

| | | | |
|---|---|---|---|
| 4,229,449 A | 10/1980 | Melloni et al. | 424/248.58 |
| 4,596,807 A | 6/1986 | Crosby | 514/277 |
| 5,068,433 A | 11/1991 | Melloni et al. | 564/349 |
| 5,192,751 A | 3/1993 | Thor | |
| 5,281,624 A | 1/1994 | Gehlert et al. | |
| 5,391,735 A | 2/1995 | Melloni et al. | 544/174 |
| 5,441,985 A | 8/1995 | Foreman | |
| 5,744,474 A | 4/1998 | Thor | |
| 5,922,914 A | 7/1999 | Gage et al. | |
| 5,998,430 A | 12/1999 | Schwantes et al. | |
| 6,028,070 A | 2/2000 | Heiligenstein | |
| 6,046,193 A | 4/2000 | Hieiligenstein | 514/239.2 |
| 6,066,643 A | 5/2000 | Perry | |

FOREIGN PATENT DOCUMENTS

| | | |
|---|---|---|
| GB | 2014981 | 9/1979 |
| GB | 2167407 | 5/1988 |
| WO | WO 96/12485 | 5/1996 |
| WO | WO 97/35584 | 10/1997 |
| WO | WO 97/35586 | 10/1997 |
| WO | WO99/15163 | 4/1999 |
| WO | WO99/15176 | 4/1999 |
| WO | WO99/15177 | 4/1999 |
| WO | WO 99/20279 | 4/1999 |
| WO | WO 99/52518 | 10/1999 |
| WO | WO 99/52531 | 10/1999 |
| WO | WO 99/58130 | 11/1999 |
| WO | WO 01/26623 | 4/2001 |

OTHER PUBLICATIONS

J. Mark Ruscin and Nora E. Morgenstern, "Tolterodine Use for Symptoms of Overactive Bladder," The Annals of Pharmacotherapy, Abstract vol. 33, pp. 1073–1082 (Oct. 1999).

J.J. Schildkraut, The Catecholamine Hypothesis of Affective Disorders : A Review of Supporting Evidence, Am. J. of Psychiatry, vol. 122, pp. 509–522 (Nov. 1965).

T.H. Svensson, et al., Feedback Inhibition of Brain Noradrenaline Neurons by Tricyclic Antidepressants: a–Receptor Mediation, Science, vol. 202, pp. 1089–1091 (1978).

E. Richelson et al., Blockade by Antidepressants and Related Compounds of Biogenic Amine Uptake into Rat Brain Synaptosomes: Most Antidepressants Selectively Block Norepinephrine Uptake, Europ. J of Pharmacology, vol. 104 pp. 277–286 (1984).

C.B. Nemeroff, The Neurobiology of Depression, Scientific American (1988) (8 pages).

M. Riva et al., Effect of Reboxetine, A New Antidepressant Drug, on the Central Noradrenergic System: Behavioral and Biochemical Studies, J. Drug Dev., vol. 1, No. 4, pp. 243–253 (1989).

T. Pacholczyk et al., Expression Cloning of a Cocaine–and Antidepressant–Sensitive Human Noradrenaline Transporter, Nature, vol. 350, No. 28, pp. 350–356 (Mar. 1991).

M. Max et al., Efficacy of Desipramine in Painful Diabetic Neuropathy: A Placebo–Controlled Trial, Pain, vol. 45, pp. 3–9 (1991).

E. Richelson, Biological Basis of Depression and Therapeutic Relevance, J. Clin. Psychiatry, vol. 52, No. 6 Suppl., pp. 4–10 (Jun. 1991).

(List continued on next page.)

Primary Examiner—Dwayne C. Jones
(74) Attorney, Agent, or Firm—Marshall, Gerstein & Borun, LLP

(57) ABSTRACT

Methods and compositions for treating humans suffering from, or preventing a human from suffering, a physiological or psychiatric disease, disorder, or a condition where inhibiting reuptake of norepinephrine is a benefit are disclosed. The compositions comprise a compound having a pharmacological selectivity of serotonin ($K_i$)/norepinephrine ($K_i$) of at least about 5000. Examples of such compounds include reboxetine, and more preferably optically pure (S,S) enantiomer of reboxetine. The methods generally include administration of a therapeutic amount of such compositions. Also disclosed are preparations of a medicament from the composition, and uses of the composition in a manufacture of the medicament to treat a human suffering from, or preventing a human from suffering, a physiological or psychiatric disease, disorder, or condition.

9 Claims, No Drawings

OTHER PUBLICATIONS

M. Max et al., Effects of Desipramine Amitriptyline and Fluoxetine on Pain in Diabetic Neuropathy, New Engl. J. Med., vol. 326, No. 19, pp. 1250–1256 (1992).

B. Cusack et al., Binding Antidepressants to Human Brain Receptors: Focus on Newer Generation Compounds, Psychopharmacology, vol. 114, pp. 559–565 (1994).

M. Max, "Treatment of Post–Herpetic Neuralgia: Antidepressants," Ann. Neurol., vol. 35, Suppl., pp. s50–s53 (1994).

W. Reimann et al., "Inhibition of Spinal Noradrenaline Uptake in Rats by the Centrally Acting Analgesic Tramadol," Biochem. Pharmacol., vol. 47, No. 12, pp. 2289–2293 (1994).

C. Pellizzoni et al., Pharmacokinetics of Reboxetine in Healthy Volunteers. Single Against Repeated Oral Doses and Lack of Enzymatic Alterations, Biopharm. Drug Dispos. vol. 17. No. 7, pp. 623–633 (1996).

R.J. Baldessarini, Depression and Mania, Goodman & Gilman's The Pharmacological Basis of Therapeutics, $9^{th}$ Ed., Chapter 19, pp. 431–439, (1996).

B.E. Leonard, Noradrenaline in Basic Models of Depression, European Neuropsychopharmacology, vol. 7, Suppl. 1, pp. S11–S16 (1997).

Discussion, European Neuropsychopharmacology, vol. 7, Suppl. 1, pp. S71 (1997).

S.A. Montgomery, Is There a Role For a Pure Noradrenergic Drug in the Treatment of Depression?, Eur. Neuropsychopharmacology, vol. 7, Suppl. 1, pp. S3–S9 (1997).

S.A. Montgomery, Reboxetine: Additional Benefits to the Depressed Patient, J. Psychopharmacology (Oxf), 11:4 Abstract (1997).

I. Hindmarch, The Effects of Antidepressants on Psychomotor Function With Particular Reference to Reboxetine, Eur. Neuropsychopharmacology, Vo. 7, Suppl. 1, pp. S17–S21 (1997).

E. Frigerio et al., Pharmacokinetics of Reboxetine Enantiomers in the Dog, Chirality, vol. 9, pp. 303–306 (1997).

A. Frazer, Pharmacology of Antidepressants, J. Clinical Psychopharmacology, vol. 17, No. 2, Suppl. 1, pp. 2S–18S (1997).

B. E. Leonard, The Role of Noradrenaline in Depression: a Review, J. Psychopharmacology, vol. II, No. 4 Suppl., pp. S39–S47 (1997).

Dostert et al., Review of the Pharmacokinetics and Metabolism of Reboxetine, a Selective Noradrenaline Reuptake Inhibitor, Euro. Neuropsychopharmacol., vol. 7, Suppl. 1, pp. s23–s35 (1997).

M. Owens et al., "Neurotransmitter Receptor and Transporter Binding Profile of Antidepressants and Their Metabolites," J. Pharmacol. Exp. Ther., vol. 283, pp. 1305–1322 (1997).

D. Healy et al., The Clinical Pharmacologic Profile of Reboxetine: Does it Involve the Putative Neurobiological Substrate of Wellbeing?, J. of Affective Disorders, vol. 51, pp. 313–322 (1998).

Anonymous, Reboxetine—Another New Antidepressant, Drugs and Therapeutics Bull., 36 (11) (1998).

S.A. Montgomery, The Place of Reboxetine in Antidepressant Therapy, J. of Clinical Psychiatry, vol. 59, Suppl. 14, pp. 26–29 (1998).

G.D. Burrows et al., Antidepressant Efficacy and Tolerability of the Selective Norepinephrine Reuptake Inhibitor Reboxetine: A Review, J. Clin. Psychiatry, vol. 59, Suppl. 14, 4 pages (1998).

J. Massana, Reboxetine Versus Fluoxetine: An Overview of Efficacy and Tolerability, J. Clin. Psychiatry, vol. 59, Suppl 14, pp. 8–10 (1998).

A. Harkin et al., Activity and Onset of Action of Reboxetine and Effect of Combination With Sertraline in an Animal Model of Depression, Eur. J. of Pharmacology, pp. 1–10 (1998).

J. Massana et al., Reboxetine: A Double–Blind Comparison With Fluoxetine in Major Depressive Disorder, Int. Clin. Psychopharmacol, vol. 14, No. 2, pp. 73–80 (1999).

J.C. Fleishaker et al., Absolute Bioavailability of Reboxetine Enantiomers and Effect of Gender on Pharmacokinetics, Biopharm. Drug Dispos. vol. 20, No. 1, pp. 53–57 (1999).

K. Moore et al., "Tissue Distribution of Tramadol and Metabolites in an Overdose Fatality," Am. J. of Forensic Med. and Path., vol. 20, No. 1, pp. 98–100 (1999).

S. Kasper, From Symptoms to Social Functioning: Differential Effects of Antidepressant Therapy, International Clinical Psychopharmacology, vol. 14, Suppl. 1, pp. S27–S31 (May 1999).

International Search Report in PCT/US00/17256 dated Jul. 12, 2001.

METHOD OF TREATING CHRONIC PAIN

CROSS-REFERENCE To RELATED APPLICATIONS

This is a division of U.S. patent application Ser. No. 09/599,213 filed Jun. 22, 2000 now U.S. Pat. No. 6,465,458, which claims the benefit under 35 U.S.C. §119(e) of U.S. provisional patent application Ser. No. 60/141,968 filed Jul. 1, 1999, U.S. provisional patent application Serial No. 60/144,131 filed Jul. 16, 1999, U.S. provisional patent application Serial No. 60/158,256 filed Oct. 6, 1999, and U.S. provisional patent application Serial No. 60/170,381 filed Dec. 13, 1999, the disclosures of which are incorporated herein by reference.

BACKGROUND OF THE INVENTION

1. Field of the Invention

The present invention relates to methods of treating individuals suffering from a variety of conditions wherein inhibiting reuptake of norepinephrine provides a benefit. In particular, the present invention relates to methods of treatment comprising administration of a compound, such as (S,S) reboxetine, to an individual, wherein the compound has a high pharmacological selectivity with respect to norepinephrine reuptake sites compared to serotonin reuptake sites. The present invention also relates to a composition containing the compound and to a preparation of a medicament containing the composition.

2. Brief Description of Related Technology

Many types of depression, mental, behavioral, and neurological disorders originate from disturbances in brain circuits that convey signals using certain monoamine neurotransmitters. Monoamine neurotransmitters include, for example, norepinephrine (noradrenaline), serotonin (5-HT), and dopamine. Lower-than-normal levels of norepinephrine are associated with a variety of symptoms including lack of energy, motivation, and interest in life. Thus, a normal level of norepinephrine is essential to maintaining drive and capacity for reward.

These neurotransmitters travel from the terminal of a neuron across a small gap (i.e., the synaptic cleft) and bind to receptor molecules on the surface of a second neuron. This binding elicits intracellular changes that initiate or activate a response or change in the postsynaptic neuron. Inactivation occurs primarily by transport (i.e., reuptake) of the neurotransmitter back into the presynaptic neuron. Abnormality in noradrenergic transmission results in various types of depression, mental, behavioral, and neurological disorders attributed to a variety of symptoms including a lack of energy, motivation, and interest in life. See generally, R. J. Baldessarini, "Drugs and the Treatment of Psychiatric Disorders: Depression and Mania" in *Goodman and Gilman's The Pharmacological Basis of Therapeutics*, McGraw-Hill, NY, N.Y., pp. 432–439 (1996).

Reboxetine (i.e., 2-[(2-ethoxyphenoxy)(phenyl)methyl] morpholine) raises the concentration of physiologically active norepinephrine by preventing reuptake of norepinephrine, for example. Reboxetine is a norepinephrine reuptake inhibitor and has been shown to be effective in the short-term (i.e., less than eight weeks) and long-term treatment of depression. In fact, reboxetine has been shown to have effectiveness that is similar to fluoxetine, imipramine, and desipramine, commonly prescribed antidepressants, in both adults and elderly patients. See S. A. Montgomery, *Reboxetine: Additional Benefits to the Depressed Patient*, Psychopharmocol (Oxf) 11:4 Suppl., S9–15 (Abstract) (1997).

Antidepressant drugs are sometimes divided into "generations." The first generation included the monoamine oxidase inhibitors (such as isocarboxazid and phenylhydrazine) and tricyclic agents (such as imipramine). The second generation of antidepressant drugs included compounds such as mianserin and trazodone. The third generation has included drugs called selective reuptake inhibitors (e.g., fluoxetine, sertraline, paroxetine, and reboxetine). Those drugs were characterized by relatively selective action on only one of the three main monoamine systems thought to be involved in depression (i.e., 5-HT (serotonin), noradrenaline (norepinephrine), and dopamine). APP Textbook of Psychopharmacology (A. F. Schatzberg and C. B. Nemeroff), American Psychiatric Press, 2d. ed., (1998); Lexicon of Psychiatry, Nuerology and the Neurosciences (F. J. Ayd, Jr.) Williams and Wilkins (1995). The antidepressant efficacy of reboxetine is evidenced by its ability to prevent resperine-induced blepharospasm and hypothermia in mice, down regulation of β-adrenergic receptors and desensitization of noradrenaline-coupled adenylate cyclase. See M. Brunello and G. Racagni, "Rationale for the Development of Noradrenaline Reuptake Inhibitors," Human Psychophramacology, vol. 13, S-13–519, Supp. 13–519 (1998).

According to a survey by Brian E. Leonard, desipramine, maprotiline, and lofepramine are relatively selective norepinephrine reuptake inhibitors with proven efficacy. These materials increase brain noradrenaline and thereby function to relieve depression. Mianserin and mirtazepine also show antidepressant-like effects by increasing noradrenaline availability by means of blocking the pre-synaptic $\alpha_2$-adrenoceptors. Still further, oxaprotiline, fezolamine, and tomoxetine are potent and selective norepinephrine reuptake inhibitors that lack neurotransmitter receptor interactions and, thus, do not cause many of the side effects characteristic of classical tricyclic antidepressants. See Brian E. Leonard, "The Role of Noradrenaline in Depression: A Review," Journal of Psychopharmocology, vol. 11, no. 4 (Suppl.), pp. S39–S47 (1997).

Reboxetine also is a selective norepinephrine reuptake inhibitor, which also produces fewer of the side effects associated with the administration of classical tricyclic antidepressants. The antidepressant efficacy of reboxetine is evidenced by its ability to prevent resperine-induced blepharospasm and hypothermia in mice, down regulation of β-adrenergic receptors and desensitization of noradrenaline-coupled adenylate cyclase. See M. Brunello and G. Racagni, "Rationale for the Development of Noradrenaline Reuptake Inhibitors," Human Psychophramacology, vol. 13 (Supp.) 13–519 (1998).

Reboxetine generally is described in Melloni et al. U.S. Pat. Nos. 4,229,449, 5,068,433, and 5,391,735, and in GB 2,167,407, the disclosures of which are hereby incorporated by reference. Chemically, reboxetine has two chiral centers and, therefore, exists as two enantiomeric pairs of diastereomers, shown below as isomers (I) through (IV):

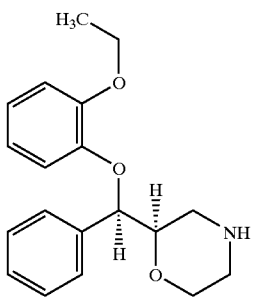

(R,R)2-[(2-ethoxyphenoxy)(phenyl)methyl]morpholine

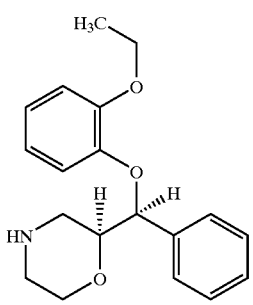

(S,S)2-[(2-ethoxyphenoxy)(phenyl)methyl]morpholine

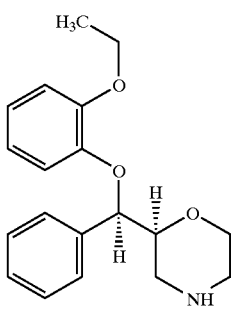

(R,S)2-[(2-ethoxyphenoxy)(phenyl)methyl]morpholine

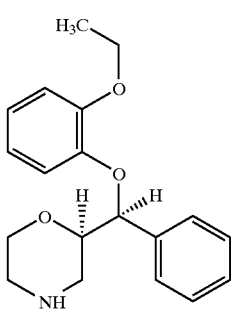

(S,R)2-[(2-ethoxyphenoxy)(phenyl)methyl]morpholine

Many organic compounds exist in optically active forms, i.e., they have the ability to rotate the plane of plane-polarized light. In describing an optically active compound the prefixes R and S are used to denote the absolute configuration of the molecule about its chiral center(s). The prefixes D and L, or (+) or (−), designate the sign of rotation of plane-polarized light by the compound, with L or (−) meaning that the compound is levorotatory. In contrast, a compound prefixed with D or (+) is dextrorotatory. There is no correlation between nomenclature for the absolute stereochemistry and for the rotation of an enantiomer. Thus, D-lactic acid is the same as (−)-lactic acid, and L-lactic acid is the same as (+)-lactic acid. For a given chemical structure, each of a pair of enantiomers are identical except that they are non-superimposable mirror images of one another. A specific stereoisomer may also be referred to as an enantiomer, and a mixture of such isomers is often called an enantiomeric, or racemic, mixture.

Stereochemical purity is important in the pharmaceutical field, where many of the most often prescribed drugs exhibit chirality. For example, the L-enantiomer of the beta-adrenergic blocking agent, propranolol, is known to be 100 times more potent than its D-enantiomer. Additionally, optical purity is important in the pharmaceutical drug field because certain isomers have been found to impart a deleterious effect, rather than an advantageous or inert effect. For example, it is believed that the D-enantiomer of thalidomide is a safe and effective sedative when prescribed for the control of morning sickness during pregnancy, whereas its corresponding L-enantiomer is believed to be a potent teratogen.

When two chiral centers exist in one molecule, there are four possible stereoisomers: (R,R), (S,S), (R,S), and (S,R). Of these, (R,R) and (S,S) are an example of a pair of enantiomers (mirror images of each other), which typically share chemical properties and melting points just like any other enantiomeric pair. The mirror images of (R,R) and (S,S) are not, however, superimposable on (R,S) and (S,R). This relationship is called diastereoisomeric, and the (S,S) molecule is a diastereoisomer of the (R,S) molecule, whereas the (R,R) molecule is a diastereoisomer of the (S,R) molecule.

Currently, reboxetine is commercially available only as a racemic mixture of enantiomers, (R,R) and (S,S) in a 1:1 ratio, and reference herein to the generic name "reboxetine" refers to this enantiomeric, or racemic, mixture. Reboxetine is commercially sold under the trade names of EDRONAX™, PROLIFT™, VESTRA™, and NOREBOX™. As previously noted, reboxetine has been shown to be useful in the treatment of human depression. Orally administered reboxetine is readily absorbed and requires once or twice a day administration. A preferred adult daily dose is in the range of about 8 to about 10 milligrams (mg). The effective daily dosage of reboxetine for a child is smaller, typically in a range of about 4 to about 5 mg. The optimum daily dosage for each patient, however, must be determined by a treating physician taking into account the patient's size, other medications which the patient may be taking, identity and severity of the particular disorder, and all of the other circumstances of the patient.

Administration of reboxetine, however, can result in undesired side effects associated with drug-drug interactions and in other undesirable effects such as, for example, dizziness, insomnia, lightheadedness, changes in blood pressure, sweating, gastrointestinal disturbances, sexual dysfunction in males, certain anticholinergic-like effects (e.g., tachyardia and urinary retention). It has been found that such side effects occur, in part, because reboxetine lacks a sufficiently high selectivity for inhibiting norepinephrine reuptake. In other words, reboxetine is blocking reuptake of other monoamines, like serotonin and dopamine, to a sufficient degree to contribute to the undesired side effects.

It has been reported that other antidepressants have a high pharmacological selectivity for inhibiting reuptake of norepinephrine. For example, oxaprotiline has a pharmacological selectivity with respect to inhibiting norepinephrine reuptake compared to serotonin reuptake of about 4166, based on a ratio of $K_i$ values. The corresponding pharmacological selectivity for desipramine is about 377, and that for maprotiline is about 446. See Elliott Richelson and Michael Pfenning, "Blockade by Antidepressants and Related Compounds of Biogenic Amine Uptake in Rat Brain Synaptosomes: Most Antidepressants Selectively Block Norepinephrine Uptake," European Journal of Pharmacology, vol. 14, pp. 277–286 (1984). Despite the relatively high selectivity of oxaprotiline, desipramine, and maprotiline, these and other known materials undesirably block receptor of other neurotransmitters to a sufficient degree that they also contribute to adverse side effects.

Accordingly, there is a need in the art for a method of treating individuals suffering from a variety of conditions where inhibiting reuptake of norepinephrine provides a benefit, while reducing or eliminating the adverse side effects associated with conventional norepinephrine reuptake inhibitors. There also is a need for a method that selectively inhibits the reuptake of norepinephrine over other neurotransmitters, like serotonin and dopamine. Specifically, there is a need in the art for a highly selective (at one reuptake site), specific (with no activity at other receptors), and potent norepinephrine reuptake inhibitor. Furthermore, there is a need for pharmaceutical compositions containing a highly selective and potent norepinephrine reuptake inhibitor. Still further, there is a need for medicaments containing such pharmaceutical compositions, and the use of such compositions in the manufacture of such medicaments.

SUMMARY OF THE INVENTION

The present invention generally is directed to compositions and methods of treating or preventing a variety of human conditions where inhibition of norepinephrine reuptake provides a benefit and, more specifically, where selective, specific, and potent inhibition of norepinephrine provides a benefit. More particularly, the present invention is directed to an effective treatment or prevention of such conditions comprising administration of compounds, such as reboxetine or an optically pure (S,S) stereoisomer thereof, to a human.

Accordingly, one embodiment of the present invention is directed to a method of selectively inhibiting reuptake of norepinephrine, the method comprising the step of administering a therapeutically effective amount of a composition to an individual, the composition comprising a compound having a pharmacological selectivity of serotonin $(K_i)$/norepinephrine $(K_i)$ of at least about 5000, preferably at least about 10,000, and more preferably at least about 12,000.

Another embodiment of the present invention is directed to a method of treating a human suffering from a condition, or preventing said condition, wherein inhibiting reuptake of norepinephrine provides a benefit, the method comprising the step of administering a therapeutically effective amount of a composition comprising a compound having a pharmacological selectivity of serotonin $(K_i)$/norepinephrine $(K_i)$ of at least about 5000, preferably at least about 10,000, and more preferably at least about 12.000.

Another embodiment of the present invention is directed to a preparation of a medicament from a composition comprising a compound having a pharmacological selectivity of serotonin $(K_i)$/norepinephrine $(K_i)$ of at least about 5000, preferably at least about 10,000, and more preferably at least about 12,000 to treat or prevent at least one nervous system disorder selected from the group consisting of addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood), age-associated learning and mental disorders (including Alzheimer's disease), anorexia nervosa, apathy, attention-deficit (or other cognitive) disorders due to general medical conditions, attention-deficit hyperactivity disorder (ADHD), bipolar disorder, bulimia nervosa, chronic fatigue syndrome, chronic or acute stress, chronic pain, conduct disorder, cyclothymic disorder, depression (including adolescent depression and minor depression), dysthymic disorder, fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder (GAD), incontinence (i.e., stress incontinence, genuine stress incontinence, and mixed incontinence), inhalation disorders, intoxication disorders (alcohol addiction), mania, migraine headaches, obesity (i.e., reducing the weight of obese or overweight patients), obsessive compulsive disorders and related spectrum disorders, oppositional defiant disorder, panic disorder, peripheral neuropathy, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), specific developmental disorders selective serotonin reuptake inhibition (SSRI) "poop out" syndrome (i.e., wherein a patient who fails to maintain a satisfactory response to SSRI therapy after an initial period of satisfactory response), and TIC disorders (e.g., Tourette's Disease).

Another embodiment of the present invention is directed to use of a composition comprising a compound having a pharmacological selectivity of serotonin $(K_i)$/norepinephrine $(K_i)$ of at least about 5000, preferably at least about 10,000, and more preferably at least about 12,000, in a manufacture of a medicament to treat or prevent at least one of the aforementioned nervous system disorders.

An example of a compound having a pharmacological selectivity of serotonin $(K_i)$/norepinephrine $(K_i)$ of at least about 5000, is optically pure (S,S) reboxetine substantially free of its (R,R) stereoisomer. Individuals treated with optically pure (S,S) reboxetine do not experience certain adverse side effects associated with the administration of the racemic mixture of (R,R) and (S,S) reboxetine. The present invention therefore includes administering optically pure (S,S) reboxetine to a human to selectively inhibit norepinephrine reuptake, and thereby control, reduce, or eliminate adverse effects caused by the administration of the racemic mixture of reboxetine.

More specifically, another embodiment of the present invention is directed to a method of treating or preventing a human condition wherein inhibiting reuptake of norepinephrine provides a benefit. The method comprises the step of administering a therapeutic amount, typically about 0.5 to about 10 mg/day, of optically pure (S,S) reboxetine, or a pharmaceutically acceptable salt thereof. Optically pure (S,S) reboxetine is substantially free of (R,R) reboxetine.

Optically pure (S,S) reboxetine is advantageous over prior treatment or prevention methods which utilized a racemic mixture of (R,R) and (S,S) reboxetine. In particular, it has been found that treatments using compositions containing an optically pure (S,S) reboxetine are about 5 to about 8.5 times more effective at inhibiting the reuptake of norepinephrine than compositions containing the racemic mixture of the (R,R) and (S,S) stereoisomers. Therefore, reuptake blockage can be achieved with much lower dosages. Accordingly, the present invention may permit a substantial reduction in the customary daily dosage of the racemic mixture (i.e., the commercially available reboxetine) by about 50% to about 80% because of the use of an optically pure (S,S) reboxetine. In addition, treatments utilizing the optically pure (S,S) reboxetine may result in fewer undesirable adverse side effects associated with the treatment because of the high selectivity and potency of (S,S) reboxetine with respect to inhibiting the reuptake of norepinephrine.

Another embodiment of the present invention is directed to a method of treating or preventing a nervous system disorder comprising the step of administering a therapeutically effective dose of racemic reboxetine to an individual, wherein the disorder is at least one of an adjustment disorder, an age-associated learning and mental disorder, anorexia nervosa, apathy, an attention-deficit disorder due to general medical conditions, bipolar disorder, bulimia nervosa, chronic fatigue syndrome, chronic or acute stress, chronic pain, cyclothymic disorder, dysthymic disorder, fibromyalgia and other somatoform disorders, incontinence, mania, migraine headaches, obesity, peripheral neuropathy, post-traumatic stress disorder, premenstrual dysphoric disorder, a psychotic disorder, seasonal affective disorder, a sleep disorders, a specific developmental disorders, SSRI "poop out" syndrome, and TIC disorders. Other embodiments of the present invention are directed to a preparation of a medicament from a composition comprising reboxetine and a use of reboxetine in a manufacture of the medicament to treat or prevent at least one of the aforementioned nervous system disorders.

Additional benefits and features of the present invention will become apparent to those skilled in the art from a review of the following detailed description, taken in conjunction with the example and the appended claims. It should be noted, however, that while the invention is susceptible of embodiments in various forms, described hereafter are specific preferred embodiments of the invention with the understanding that the present disclosure is intended as illustrative, and is not intended to limit the invention to the specific embodiments described herein.

DETAILED DESCRIPTION OF THE PREFERRED EMBODIMENTS

Reboxetine is a known compound that is active on the central nervous system, and has been used as an antidepressant. Heretofore, use of reboxetine has been limited to the treatment of depression, oppositional defiant disorder, attention-deficit/hyperactivity disorder, and conduct disorder. These proposed treatments are disclosed in International Publication Nos. WO 99/15163, WO 95/15176, and WO 99/15177. These treatment methods are limited to administration of a racemic mixture of the (S,S) and (R,R) reboxetine stereoisomers.

Reboxetine does not act like most antidepressants. Unlike tricyclic antidepressants, and even selective serotonin reuptake inhibitors (SSRIs), reboxetine is ineffective in the 8-OH-DPAT hypothermia test, indicating that reboxetine is not a SSRI. Brian E. Leonard, "Noradrenaline in basic models of depression." *European-Neuropsychopharmacol*, 7 Suppl. 1 pp. S11–6 and S71–3 (April 1997). Reboxetine is a selective norepinephrine reuptake inhibitor, with only marginal serotonin and no dopamine reuptake inhibitory activity. Reboxetine displays no anticholinergic binding activity in different animal models, and is substantially devoid of monoamine oxidase (MAO) inhibitory activity. Racemic reboxetine exhibits a pharmacological selectivity of serotonin ($K_i$)/norepinephrine ($K_i$) of about 80. The $K_i$ values are discussed in more detail hereafter.

Another embodiment of the present invention includes a method of selectively inhibiting reuptake of norepinephrine, the method comprising the step of administering a therapeutically effective amount of a composition to an individual, the composition comprising a compound having a pharmacological selectivity of serotonin ($K_i$)/norepinephrine ($K_i$) of at least about 5000, preferably at least about 10,000, and more preferably at least about 12,000.

Another embodiment of the present invention is directed to a composition comprising a compound having a pharmacological selectivity of serotonin ($K_i$)/norepinephrine ($K_i$) of at least about 5000, preferably at least about 10,000, and more preferably at least about 12,000. The inventive composition is useful in the treatment or prevention of diseases, disorders, and conditions (described in more detail below) wherein inhibition of reuptake of norepinephrine is beneficial. An example of such a compound is an optically pure (S,S) stereoisomer of reboxetine, or a pharmaceutically effective salt thereof.

To determine the degree of selectivity of a compound to bind to the norepinephrine reuptake site, the inhibition constant (or $K_i$ value) of the compound for serotonin reuptake site was divided by the $K_i$ value for norepinephrine reuptake site. A lower value of $K_i$ for norepinephrine reuptake indicates greater binding affinity to norepinephrine receptors. A higher serotonin ($K_i$)/norepinephrine ($K_i$) ratio indicates a greater selectivity for binding the norepinephrine receptor. Accordingly, the present invention is directed to a composition comprising a compound having a pharmacological selectivity of serotonin ($K_i$)/norepinephrine ($K_i$) of at least about 5000, preferably at least about 10,000, and more preferably at least about 12,000, as noted above. Furthermore, it is envisioned that selectivity values far in excess of 12,000, such as 25,000, 50,000, 75,000. and even up to 100,000 or greater, also are beneficial.

The compositions of the present invention, when employed in effective amounts in accordance with the present invention, are selective with respect to the norepinephrine reuptake site, but do not cause significant blockade of receptors associated with undesirable side effects e.g., serotonin and dopamine receptors. In other words, a dose of the inventive composition capable of inhibiting the reuptake of norepinephrine, is essentially ineffective in eliciting blockade of other neurotransmitter receptors. Inhibition constants ($K_i$ values), typically reported in units of nanamolars (nM), were calculated from the $IC_{50}$ values according to the method set forth in Y. C. Cheng and W. H. Prusoff, "Relationship Between the Inhibitory Constant ($K_i$) and the Concentration of Inhibitor Which Causes 50% Inhibition ($IC_{50}$) of an Enzymatic Reaction," Biochemical Pharmacology, vol. 22, pp. 3099–3108 (1973).

Another embodiment of the present invention is directed to an effective method using an optically pure (S,S) stereoisomer of reboxetine to treat or prevent conditions wherein inhibition of reuptake of norepinephrine is beneficial. (S,S)

Reboxetine is an effective, selective inhibitor of norepinephrine reuptake and, accordingly, dose levels can be substantially reduced in comparison to racemic reboxetine. In addition, individuals treated with an optically pure (S,S) reboxetine do not experience certain adverse effects associated with the administration of the racemic mixture of (R,R) and (S,S) reboxetine. Accordingly, another embodiment of the present invention includes administering a therapeutic amount of an optically pure (S,S) reboxetine to a human to inhibit the reuptake of norepinephrine, and to control, reduce, or eliminate adverse effects associated with administration of racemic reboxetine.

Yet another embodiment of the present invention is directed to a method of treating or preventing a human condition wherein inhibiting reuptake of norepinephrine provides a benefit. The method comprises the step of administering, and preferably orally administering, a total dose of about 0.1 mg/day to about 10 mg/day, more preferably about 0.5 to about 10 mg/day of an optically pure (S,S) reboxetine, or a pharmaceutically acceptable salt thereof, to an individual.

As used herein, the term "reboxetine" refers to the racemic mixture of the (R,R) and (S,S) enantiomers of reboxetine. In contrast, the term "(S,S) reboxetine" refers to only the (S,S) stereoisomer. Similarly, the term "(R,R) reboxetine" refers to only the (R,R) stereoisomer.

The phrases "optically pure (S,S) reboxetine" and "substantially free of its (R,R) stereoisomer," as used herein, mean that the composition contains a greater proportion of (S,S) reboxetine in relation to (R,R) reboxetine. In a preferred embodiment, the phrases mean that the composition is at least 90 percent by weight (wt. %) of (S,S) reboxetine, and 10 wt. % or less of (R,R) reboxetine. In a more preferred embodiment the phrases mean that the composition contains at least 97 wt. % of (S,S) reboxetine, and 3 wt. % or less of (R,R) reboxetine. In an even more preferred embodiment, the phrases mean that the composition contains at least 99 wt. % of (S,S) reboxetine, and 1 wt. % or less of (R,R) reboxetine. In a most preferred embodiment, the phrases "optically pure (S,S) reboxetine" and "substantially free of its (R,R) stereoisomer," as used herein, mean that the composition contains greater than 99 wt. % of (S,S) reboxetine. The foregoing percentages are based upon the total amount of reboxetine present in the composition. The phrases "substantially free of (R,R) reboxetine," "substantially optically pure (S,S) stereoisomer of reboxetine," "substantially optically pure (S,S) reboxetine," "optically pure (S,S) stereoisomer of reboxetine," and "optically pure (S,S) reboxetine" are also encompassed by the above-described amounts.

The phrases "pharmaceutically acceptable salts" or "a pharmaceutically acceptable salt thereof" refer to salts prepared from pharmaceutically acceptable acids or bases, including organic and inorganic acids and bases. Because the active compound (i.e. (S,S) reboxetine) used in the present invention is basic, salts may be prepared from pharmaceutically acceptable acids. Suitable pharmaceutically acceptable acids include acetic, benzenesulfonic (besylate), benzoic, p-bromophenylsulfonic, camphorsulfonic, carbonic, citric, ethanesulfonic, fumaric, gluconic, glutamic, hydrobromic, hydrochloric, hydroiodic, isethionic, lactic, maleic, malic, mandelic, methanesulfonic (mesylate), mucic, nitric, oxalic, pamoic, pantothenic, phosphoric, succinic, sulfuric, tartaric, p-toluenesulfonic, and the like. Examples of such pharmaceutically acceptable salts of (S,S) reboxetine, thus, include, but are not limited to, acetate, benzoate, β-hydroxybutyrate, bisulfate, bisulfite, bromide, butyne-1,4-dioate, carpoate, chloride, chlorobenzoate, citrate, dihydrogenphosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, methylbenzoate, monohydrogenphosphate, naphthalene-1-sulfonate, naphthalene-2-sulfonate, oxalate, phenylbutyrate, phenylproionate, phosphate, phthalate, phylacetate, propanesulfonate, propiolate, propionate, pyrophosphate, pyrosulfate, sebacate, suberate, succinate, sulfate, sulfite, sulfonate, tartrate, xylenesulfonate, and the like. A preferred pharmaceutical salt of (S,S) reboxetine is methanesulfonate (i.e., mesylate), which is prepared using methanesulfonic acid.

The phrases "side effects," "adverse effects," and "adverse side effects" in relation to reboxetine include, but are not limited to, dizziness, insomnia, lightheadedness, changes in blood pressure, gastrointestinal disturbances, sexual dysfunction in males, extrapyramidal side effects, certain anticholinergic-like effects (e.g., tachycardia, blurred vision), and undesired side effects associated with with drug-drug interactions.

As used herein, the terms "treat," "treatment," and "treating," refer to: (a) preventing a disease, disorder, or condition from occurring in a human which may be predisposed to the disease, disorder and/or condition but has not yet been diagnosed as having it; (b) inhibiting the disease, disorder, or condition, i.e., arresting its development; and (c) relieving the disease, disorder, or condition, i.e., causing regression of the disease, disorder and/or condition. In other words, the terms "treat," "treatment," and "treating," extend to prophylaxis, in other words "prevent," "prevention," and "preventing," as well as treatment of established conditions. Accordingly, use of the terms "prevent," "prevention," and "preventing," would be an administration of the pharmaceutical composition to a person who has in the past suffered from the aforementioned conditions, such as, for example, migraine headaches, but is not suffering from the conditions at the moment of the composition's administration. For the sake of simplicity, the term "conditions" as used hereinafter encompasses conditions, diseases, and disorders.

Methods and compositions of the present invention are useful in treating a human condition wherein inhibiting reuptake of norepinephrine provides a benefit. The method comprises the step of administering, and preferably orally administering, a sufficient amount of the inventive composition to provide a total dose of about 0.1 to about 10 mg/day of the selective compound to an individual.

More specifically, administration of the inventive composition (e.g., a composition containing an optically pure (S,S) reboxetine) is effective in treating various human conditions including, but not limited to, addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood), age-associated learning and mental disorders (including Alzheimer's disease), anorexia nervosa, apathy, attention-deficit (or other cognitive) disorders due to general medical conditions, attention-deficit hyperactivity disorder (ADHD), bipolar disorder, bulimia nervosa, chronic fatigue syndrome, chronic or acute stress, chronic pain, conduct disorder, cyclothymic disorder, depression (including adolescent depression and minor depression), dysthymic disorder, fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder (GAD), incontinence (i.e., stress incontinence, genuine stress incontinence, and mixed incontinence), inhalation disorders, intoxication disorders (alcohol addiction), mania, migraine headaches, obesity (i.e., reducing the weight of obese or overweight patients), obsessive compulsive disorders and related spectrum disorders, oppositional defiant disorder, panic disorder, peripheral neuropathy, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), specific developmental disorders, selective serotonin reuptake inhibition (SSRI) "poop out" syndrome (i.e., wherein a patient who fails to maintain a satisfactory response to SSRI therapy after an initial period of satisfactory response), and TIC disorders (e.g., Tourette's Disease).

The administration of the inventive composition is very effective in the treatment of addictive disorders and withdrawal syndromes, adjustment disorders, apathy, attention-deficit hyperactivity disorder, attention-deficit disorders due to medical conditions, bulimia nervosa, chronic fatigue syndrome, chronic or acute stress, depression, dysthymic disorder, generalized anxiety disorder (GAD), nicotine addiction, panic disorder, post-traumatic stress disorder, premenstrual dysphoric disorder, schizoaffective disorder, and SSRI "poop out" syndrome. Furthermore, the administration of (S,S) reboxetine is especially effective in treatment or prevention of addictive disorders and withdrawal syndromes, apathy, attention-deficit hyperactivity disorder, attention-deficit disorders due to medical conditions, chronic fatigue syndrome, chronic or acute stress, dysthymic disorder, depression, nicotine addiction, obesity, post-traumatic stress disorder, and SSRI "poop out" syndrome.

Reference to treatments for "nicotine addiction" herein also includes treatments for smoking cessation. Many of the foregoing human conditions are generally described by the American Psychiatric Association in their publication entitled, "Diagnostic and Statistical Manual of Mental Disorders," 4th ed. rev. (Washington D.C. 1994), the disclosure of which is hereby incorporated by reference. General descriptions of addictive disorders, including disorders related to intoxication and inhalants and, and nicotine addiction may be found in many standard references, such as R. E. Hales et al., "The American Psychiatric Press Textbook of Psychiatry," 3d. ed. (1999), the disclosure of which is hereby incorporated by reference.

An inventive composition also can be used to treat migraine headaches. Furthermore, the inventive composition can be used to treat headaches in migraineurs or people suffering from migraine headaches, including the treatment of symptoms of an existing headache, treatment to prevent the occurrence, intensity, and duration of a headache, prophylactic use to prevent or reduce the incidence or duration of migraines, as an adjuvant to facilitate the effectiveness of an abortive medication or co-administered with other medications (including abortive medications) to reduce the required dosages (and side effects) of those medications.

A preferred embodiment of the inventive composition includes (S,S) reboxetine. It is known that commercially-available reboxetine is a racemic mixture of the (R,R) and (S,S) enantiomers of 2-[(2-ethoxyphenoxy)(phenyl)methyl] morpholine. It has now been discovered that the (S,S) stereoisomer is the most active and the most selective stereoisomer with respect to inhibiting the reuptake of norepinephrine. In addition, when administered to an individual, in the dosages described herein, as an optically pure material (i.e., in the substantial absence of its (R,R) diastereomer), the individual does not experience many of the adverse side effects associated with the administration of commercially-available reboxetine. Furthermore, it has further been discovered that the (S,S) and (R,R) enantiomers have a reversed selectivity for the norepinephrine neurotransmitter in relation to the serotonin neurotransmitter, and an optically pure (S,S) reboxetine is significantly more effective at inhibiting reuptake of norepinephrine than either the (R,R) enantiomer or a racemic mixture of the (S,S) and (R,R) enantiomers.

Specifically, it has been found that compositions containing an optically pure (S,S) reboxetine are about 5 to about 8.5 times more effective at inhibiting the reuptake of norepinephrine than compositions containing the racemic mixture of the (R,R) and (S,S) stereoisomers. Accordingly, the typical daily dosage of the racemic mixture (i.e., commercially available reboxetine) can be reduced by about 50% to about 80% when using an optically pure (S,S) reboxetine. The reduction in dosage does not lead to a reduction in efficacy, but the reduction or elimination of various adverse side effects was observed.

In particular, because an optically pure (S,S) reboxetine selectively inhibits norepinephrine reuptake compared to serotonin reuptake, adverse side effects associated with serotonin reuptake are reduced or eliminated. Such adverse side effects include, but are not limited to, gastrointestinal disturbances, anxiety, sexual dysfunction, and undesirable side effects associated with drug-drug interactions.

The synthesis of a racemic mixture of reboxetine is disclosed in Melloni et al. U.S. Pat. No. 4,229,449. Individual stereoisomers of reboxetine can be obtained by resolution of the racemic mixture of enantiomers using conventional methods generally known by those skilled in the art. Such methods include, but are not limited to, resolution by simple crystallization and chromatographic techniques, for example, as set forth in GB 2,167,407.

While it is possible to administer a highly selective norepinephrine reuptake inhibitor directly without any formulation, a composition preferably is administered in the form of pharmaceutical medicaments comprising the selective norepinephrine reuptake inhibitor. The inventive composition can be administered in oral unit dosage forms such as tablets, capsules, pills, powders, or granules. The inventive composition also can be introduced parenterally, (e.g., subcutaneously, intravenously, or intramuscularly), using forms known in the pharmaceutical art. The inventive composition further can be administered rectally or vaginally in such forms as suppositories or bougies. The inventive composition also can be administered topically or transdermally, such as with a "patch" containing active ingredient. Transdermal delivery patches can be used to provide continuous, pulsatile, or on-demand infusion of the inventive compositions in controlled amounts. The construction and use of transdermal delivery patches are well known in the pharmaceutical art, and are described, for example, in U.S. Pat. Nos. 3,742,951, 3,742,951, 3,797,494, 3,996,934, 4,031,894, and 5,023,252.

It may be desirable or necessary to introduce the inventive composition or pharmaceutical compositions containing the selective norepinephrine reuptake inhibitor to the brain, either directly or indirectly. Direct techniques usually involve placement of a suitable drug delivery catheter into the ventricular system to bypass the blood-brain barrier. One such suitable delivery system used for the transport of biological factors to specific anatomical regions of the body is described in U.S. Pat. No. 5,011,472, the disclosure of which is incorporated herein by reference.

In general, the preferred route of administering the inventive composition is oral, with a once or twice a day administration. The dosage regimen and amount for treating patients with the inventive composition is selected in accordance with a variety of factors including, for example, the type, age, weight, sex, and medical condition of the patient, the severity of the condition, the route of administration and the particular compound employed, either racemate or pure enantiomer. An ordinarily skilled physician or psychiatrist can readily determine and prescribe an effective (i.e., therapeutic) amount of the compound to prevent or arrest the progress of the condition. In so proceeding, the physician or psychiatrist could employ relatively low dosages at first, subsequently increasing the dose until a maximum response is obtained.

Pharmaceutical compositions suitable for oral administration can be of any convenient form, such as sachets, tablets, capsules, pills, or aerosol sprays, each containing a predetermined amount of the active compound either as a powder or granules, or as a solution or a suspension in an aqueous liquid, a non-aqueous liquid, an oil-in-water emulsion, or a water-in-oil liquid emulsion. Such compositions can be prepared by any method that includes the step of bringing the active compound either into intimate association with a carrier, which constitutes one or more necessary or desirable ingredients. Generally, the compositions are prepared by uniformly and intimately admixing the active ingredient with liquid carriers or finely divided solid carriers or both, and then, if necessary, shaping the product into a desired form.

For example, a tablet can be prepared by compression or molding techniques, optionally, using one or more accessory ingredients. Compressed tablets can be prepared by compressing the active ingredient in a suitable machine into a free-flowing form, such as a powder or granules. Thereafter, the compressed, free-flowing form optionally can be mixed with a binders, diluents, lubricants, disintegrating agents, effervescing agents, dyestuffs, sweeteners, wetting agents, and non-toxic and pharmacologically inactive substances typically present in pharmaceutical compositions. Molded tablets can be made by molding a mixture of the powdered compound moistened with an inert liquid diluent in a suitable machine.

Suitable binders for use in the pharmaceutical preparation include, for example, starches, gelatine, methylcellulose, gum arabic, tragacanth, and polyvinylpyrrolidone. Suitable diluents for use in the pharmaceutical preparation include, for example, lactose, dextrose, sucrose, mannitol, sorbitol, and cellulose. Suitable lubricants for use in the pharmaceutical preparation include, for example, silica, talc, stearic acid, magnesium or calcium stearate, and or polyethylene glycols. Suitable disintegrating agents for use in the pharmaceutical preparation include, for example, starches, alginic acid, and alginates. Suitable wetting agents for use in the pharmaceutical preparation include, for example, lecithin, polysorbates, and laurylsulfates. Generally, any effervescing agents, dyestuffs, and/or sweeteners known by those of ordinary skill in the art can be used in the preparation of a pharmaceutical composition.

Desirably, daily dose of the composition (e.g., tablet, sachet, or capsule) contains from about 0.1 to about 10 mg of optically pure (S,S) reboxetine, and is substantially free of its (R,R) stereoisomer. More preferably, each dose of the composite contains about 0.5 to about 8 mg of the active ingredient, optically-pure (S,S) reboxetine, and is substantially free of its (R,R) stereoisomer. Even more preferably, however, each dose contains from about 0.5 to about 5 mg of the active ingredient, such as an optically-pure (S,S) reboxetine, and is substantially free of its (R,R) stereoisomer. This dosage form permits the full daily dosage of about 0.5 to about 2.5 mg to be administered in one or two oral doses. This will allow for tablets containing 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9. 2.0, 2.1, 2.2, 2.3, 2.4, or 2.5 mg of optically pure (S,S) reboxetine.

In another embodiment, a preferred daily dose of the composition (e.g., tablet, sachet, or capsule) contains from about 0.1 to about 0.9 mg of optically pure (S,S) reboxetine, and is substantially free of its (R,R) stereoisomer. More preferably, each dose of the composition contains about 0.5 to about 0.8 mg of the active ingredient, optically-pure (S,S) reboxetine, and is substantially free of its (R,R) stereoisomer. Even more preferably, however, each dose contains from about 0.5 to about 0.75 mg of the active ingredient, optically pure (S,S) reboxetine, and is substantially free of its (R,R) stereoisomer. This dosage form permits the full daily dosage of about 0.5 to about 0.9 mg to be administered in one oral dose.

Patients suffering from depression, nicotine addiction, conduct disorder, oppositional defiant disorder, and/or attention-deficit hyperactivity disorder will benefit from the administration of the inventive composition, and specifically one containing an optically pure (S,S) reboxetine, regardless of these or other co-morbid conditions. Diagnostic criteria for these disorders generally are provided by the American Psychiatric Association and published in their "Diagnostic and Statistical Manual of Mental Disorders," 4th ed. rev. (Washington D.C. 1994), and in International Publication Nos. WO 99/15177, WO 99/15176, and WO 99/15163, the disclosures of which are hereby incorporated by reference.

Furthermore, patients suffering from addictive disorders and withdrawal syndromes, adjustment disorders, apathy, attention-deficit hyperactivity disorder, attention-deficit disorders due to medical conditions, bulimia nervosa, chronic fatigue syndrome, chronic or acute stress, depression, dysthymic disorder, generalized anxiety disorder (GAD), nicotine addiction, panic disorder, post-traumatic stress disorder, premenstrual dysphoric disorder, schizoaffective disorder, and SSRI "poop out" syndrome will benefit from the administration of the inventive composition, and specifically one containing optically pure (S,S) reboxetine.

These disorders display similar patterns in children, adolescents, and adults. Hence, methods of the present invention are effective in the treatment of child, adolescent, and adult patients. For purposes of the present invention, a child is considered to be a person below the age of puberty, an adolescent is considered to be a person between the age of puberty and up to about 18 years of age, and an adult generally is a person of at least about 18 years of age. As previously noted, the optimum daily dosage for each patient must be determined by a treating physician taking into account each patient's size, other medications which the patient is taking, identity and severity of the disorder, and all of the other circumstances of the patient.

As stated above, reboxetine acts as an antidepressant. Reboxetine, however, does not act like most antidepressants. Unlike trycyclic antidepressants, and even selective serotonin reuptake inhibitors (SSRIs), reboxetine is ineffective in the 8-OH-DPAT hypothermia test, indicating that reboxetine is not a selective serotonin reuptake inhibitor. Rather, reboxetine is selective for the noradrenergic system. Reboxetine is not an SSRI, but is a novel, selective, noradrenaline reuptake inhibitor (NR1). B. Leonard, "Noradrenaline in basic models of depression." *European-Neuropsychopharmacol,* 7 Suppl. 1 pp. S11–6 and S71–3 (April, 1997). Unlike most prior generation drugs, reboxetine is a highly selective norepinephrine reuptake inhibitor, with only marginal serotonin and no dopamine reuptake inhibitory activity. Reboxetine displays no anticholinergic binding activity in different animal models, and is devoid of monoamine oxidase (MAO) inhibitory activity.

Reboxetine also is a highly potent, pharmacologically specific, and fast acting agent. Investigations indicate that reboxetine has potent antireserpine activity, and combines the inhibitory properties of classical tricyclic antidepressants on the reuptake of noradrenaline with an ability to desensitize β-adrenergic receptor function, without showing any appreciable blocking action at muscarinic, cholinergic, histaminergic, and α-adrenergic receptors. Moreover, reboxetine shows less vagolytic activity than tricyclic antidepressants, and no evidence of cardiotoxicity.

Accordingly, in another embodiment of the invention, racemic reboxetine can be used to treat or prevent a number of mental and neurological disorders. Specifically, reboxetine has been found particularly useful for treating or enhancing the treatment or prevention of a variety of psychiatric symptoms or disorders, with greater efficacy and with fewer side effects than with treatment by known drugs. Furthermore, reboxetine may also be used to treat, or to enhance the treatment or prevention of other specific psychiatric symptoms or disorders.

Mental and neurological disorders that may be treated or prevented by administration of a therapeutically effective amount of a racemic reboxetine (or a derivative or pharmaceutically acceptable salts thereof) include, but are not limited to adjustment disorders (including depressed mood, anxiety, mixed anxiety and depressed mood, disturbance of conduct, and mixed disturbance of conduct and mood), age-associated learning and mental disorders (including Alzheimer's disease), anorexia nervosa, apathy, attention-deficit (or other cognitive) disorders due to general medical conditions, bipolar disorder, bulimia nervosa, chronic fatigue syndrome, chronic or acute stress, chronic pain, cyclothymic disorder, dysthymic disorder, fibromyalgia and other somatoform disorders (including somatization disorder, conversion disorder, pain disorder, hypochondriasis, body dysmorphic disorder, undifferentiated somatoform disorder, and somatoform NOS), incontinence (i.e., stress incontinence, genuine stress incontinence, and mixed incontinence), mania, migraine headaches, obesity (i.e., reducing the weight of obese or overweight patients), peripheral neuropathy, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), specific developmental disorders, selective serotonin reuptake inhibition (SSRI) "poop out" syndrome, and TIC disorders (e.g., Tourette's Disease).

Similar to (S,S) reboxetine, racemic reboxetine also can be used to treat humans suffering from migraine headaches, paticularly to reduce the frequency, duration, intensity, and or complications resulting from migraine headaches. Furthermore, racemic reboxetine can be used to prevent migraine headaches.

Additionally, racemic reboxetine can be used to treat incontinence (i.e., stress incontinence, genuine stress incontinence, and mixed incontinence). Stress urinary incontinence is a symptom describing involuntary loss of urine on carrying out any activity that raises intra-abdominal pressure such as coughing or sneezing. Stress incontinence is also a clinical sign, that is the observation by a care giver of a jet of urine escaping from the urethral meatus (opening) when the patient coughs or strains. Genuine Stress Incontinence is the pathological diagnosis of an incompetent urethral sphincter as diagnosed by Urodynamic testing. Mixed incontinence is stress incontinence in combination with urge incontinence. The latter is a part of the symptom complex of the Overative Bladder. Retention may be due to outflow obstruction (e.g., high urethral pressure), poor detrusor (bladder muscle) contractility or lack of coordination between detrusor contraction and urethral relaxation.

The racemate form of reboxetine is well tolerated and has a wide safety range. Racemic reboxetine can be administered to an individual in an amount in a range of about 2 to about 20 milligrams per patient per day (mg/day), and preferably about 4 to about 10 mg/day, and more preferably about 6 to about 10 mg/day. Depending upon the formulation and the individual's disorder, the total daily dosage can be administered in small amounts up to two times a day. Reboxetine typically is administered orally, for example, in the form of tablets, but can be adminstered parentally, transdermally, rectally, or vaginally.

A preferred method of administering racemic reboxetine is oral dosing once or twice a day. It can also be administered at dosages of about 2, 4, 6, 8, 10, or 12 mg/day or fractions thereof. For example, suitable administrations could be about 4 mg in the morning and about 2 or about 4 mg in the afternoon or evening. In some patients, the ideal dosing would be about 3 to about 5 mg in the morning and about 3 to about 5 mg in the afternoon. A skilled physician or psychiatrist can determine the precise level of dosing. The ideal dosing is routinely determined by an evaluation of clinical trials and the needs of specific patients.

In accordance with the present invention, the racemic reboxetine also can be administered as the free base or a pharmaceutically acceptable salt thereof. The phrases "pharmaceutically acceptable salts" or "a pharmaceutically acceptable salt thereof" refer to salts prepared from pharmaceutically acceptable acids or bases, including organic and inorganic acids and bases as described above with respect to the salts of optically pure (S,S) reboxetine. A preferred pharmaceutical salt of reboxetine is methanesulfonate (i.e., mesylate), which is prepared using methanesulfonic acid.

Treatment or prevention of above disorders involves the administration of reboxetine in a manner and form that result in a reduction in the symptoms of the disease or disorder. Typically, the symptoms exhibited by children, adolescents, and adults are similar to each other. Hence, as noted above, methods of the present invention are effective in the treatment of child, adolescent, and adult patients.

EXAMPLE

This example demonstrates the superior pharmacological selectivity and potency of a composition according to the present invention. More specifically, this example demonstrates the superior pharmacological selectivity and potency of (S,S) reboxetine compared to its (R,R) stereoisomer and to racemic reboxetine.

Sprague-Dawley rats weighing about 250 to about 300 grams (g) were decapitated, and cerebral cortical tissue was removed immediately. Cerebral cortices were homogenized in nine volumes of medium each containing 0.32 molar (M) sucrose using a rotating pestle. The obtained homogenate was centrifuged at about 1000×g for about 10 minutes at about 4° C. A supernatant was collected and further centrifuged at about 20,000×g for about 20 minutes at a temperature of about 4° C. A protein pellet resulting from the centrifuge steps was re-suspended in a Kreb's-Hepes buffer to result in a protein concentration of about 2 mg/ml of buffer. The buffer was maintained at a pH of about 7.0 and contained: 20 mM Hepes; 4.16 mM $NaHCO_3$; 0.44 mM $KH_2PO_4$; 0.63 mM $NaH_2PO_4$; 127 mM NaCl; 5.36 mM KCl; 1.26 mM $CaCl_2$; and 0.98 mM $MgCl_2$.

Protein/buffer suspension was introduced into 166 assay tubes such that about 30 $\mu$g ($10^{-6}$ grams) to about 150 $\mu$g of the protein was added to each of 166 assay tubes (i.e., 80 assays per transporter assay). Binding to serotonin and norepinephrine reuptake sites was determined as follows. Synaptosomal uptake of $^3$H-norpinephrine was determined as follows. About 1.4 nanomolar of [$^3$H]citalopram and about 1.9 nM of [$^3$H]nisoxetine were used to label serotonin and norepinephrine reuptake sites, respectively. Nonspecific binding was defined by 100 micromolar ($\mu$M) fluoxetine (for serotonin) and 10 $\mu$M desipramine (for norepinephrine). Incubation in total assay volume of about 500 microliters ($\mu$l) was carried out for about 60 minutes (for serotonin) and 120 minutes (for norepinephrine). Both incubations were carried out at about 25° C., and terminated by rapid filtration through a 48-well cell harvester though GFB filters (pre-soaked with about 0.5 PEI for about 4 hours) in a 3×5 ml of ice-cold 200 mM tris-HCl, pH 7.0. Punched-out filters were placed into 7 ml minivials and radioactive assayed by liquid scintillation counting.

The ability of reboxetine (i.e., racemic mixture of (R,R) and (S,S) reboxetine), (R,R) reboxetine, and (S,S) reboxetine to bind to norepinephrine and serotonin reuptake sites was evaluated in binding assays using the two radioligands, [$^3$H]citalopram and [$^3$H]nisoxetine. The concentration of the test compound required to inhibit 50% of the specific binding at the two reuptake sites ($IC_{50}$ values) were determined by non-linear least square regression analysis. A conversion of $IC_{50}$ values to $K_i$ values was performed using the Cheng-Prassoff equation presented below:

$$K_i = IC_{50}/(1+([L]/[K_d \text{ of } L])),$$

wherein [L] is the radioligand concentration used in nM, and $K_d$ is the binding affinity of L in nM. See Y. C. Cheng and W. H. Prusoff, "Relationship Between the Inhibitory Constant ($K_i$) and the Concentration of Inhibitor Which Causes 50% Inhibition ($IC_{50}$) of an Enzymatic Reaction," Biochemical Pharmacology, vol. 22, pp. 3099–3108 (1973).

The $K_i$ values calculated according to the Cheng-Prassoff equation are provided in the table below:

TABLE

| Compound | Norepinephrine Reuptake ($K_i$ nM) | Serotonin Reuptake ($K_i$ nM) | Selectivity of $K_i$ of Serotonin/ Norepinphrine |
|---|---|---|---|
| (S,S) Reboxetine | 0.23 ± 0.06 | 2937 ± 246 | 12,770 |
| (R,R) Reboxetine | 7.0 ± 1.7 | 104 ± 43 | 15 |
| Reboxetine | 1.6 ± 0.6 | 129 ± 13 | 81 |

The data shows that (S,S) reboxetine is about five to about eight fold more potent than the reboxetine racemate with respect to inhibiting the reuptake of norepinephrine. In addition, racemic reboxetine has an 81 fold selectivity favoring norepinephrine reuptake inhibition over serontonin reuptake inhibition. Unexpectedly, the enantiomeric selectivity of the (S,S) and (R,R) reboxetine stereoisomers with respect to inhibiting the reuptake of norepinephrine and serotonin are quite different. The (S,S) enantiomer is very poor with respect to inhibiting reuptake of serotonin (i.e., a high $K_i$) and, therefore, has a surprisingly high selectivity for the norepinephrine reuptake site. In particular, the selectivity of serotonin versus norepinephrine increases from 81 (for the racemate) to 12,770 for an optically pure (S,S) reboxetine. Accordingly, administration of a therapeutic dose of (S,S) reboxetine effectively inhibits nonepinephrine reuptake, but serotonin reuptake essentially is not affected. Likewise, there is a further increase in separation between the action on norepinephrine reuptake sites and at other receptors. As a consequence, adverse side effects associated with the inhibition of serotonin reuptake and blockade at other receptors are not manifested.

Surprisingly, this effect is not observed with (R,R) reboxetine, but are quite to the contrary. (R,R) reboxetine is a weaker inhibitor than (S,S) reboxetine with respect to nonepinephrine reuptake, i.e., affinity ($K_i$) for (R,R) reboxetine is 7 nM whereas the $K_i$ for (S,S) reboxetine is 0.23 mM. In addition, (R,R) reboxetine is much more effective at inhibiting serotonin uptake than (S,S) reboxetine, i.e., $K_i$ for (R,R) reboxetine is 104 nM, whereas the $K_i$ for (S,S) reboxetine is 2937 nM. Accordingly, (R,R) reboxetine has a low selectivity for nonepinephrine reuptake inhibition versus serotonin reuptake inhibition.

The surprisingly high potency of the (S,S) enantiomer over both the racemic reboxetine and (R,R) reboxetine provides a treating physician an ability to prescribe an effective dosage of a norepinephrine reuptake inhibitor, i.e., (S,S) reboxetine, that is about 10% to about 20% of the current daily dosage of reboxetine (racemate) to achieve the same reuptake inhibition at the norepinephrine site. In addition, the surprisingly high inhibition selectivity of an optically pure (S,S) reboxetine essentially limits inhibition to norepinephrine reuptake, thereby reducing adverse side effects associated with inhibition at serotonin reuptake sites and blockade at other receptors.

The foregoing description is given for clearness of understanding only, and no unnecessary limitations should be understood therefrom, as modifications within the scope of the invention may be apparent to those having ordinary skill in the art.

What is claimed is:

1. A method of treating chronic pain, the method comprising the step of administering a therapeutically effective dose of racemic reboxetine or a pharmaceutically acceptable salt thereof to an individual.

2. The method of claim 1 wherein the reboxetine is administered to the individual in an amount of about 2 to about 20 mg/day.

3. The method of claim 2 wherein the reboxetine is administered to the individual in an amount of about 4 to about 10 mg/day.

4. The method of claim 3 wherein the reboxetine is administered to the individual in an amount of about 6 to about 10 mg/day.

5. The method of claim 1 wherein said reboxetine is administered orally, parenterally, topically, transdermally, rectally, or vaginally.

6. The method of claim 5 wherein said reboxetine is orally administered with a pharmaceutically acceptable carrier comprising at least one of a binder, diluent, lubricant, disintegrating agent, effervescing agent, dyestuff, sweetener, and wetting agent.

7. The method of claim 6 wherein the oral administration is by a sachet, capsule, tablet, or aerosol spray.

8. The method of claim 7 wherein said reboxetine is parentarally administered subcutaneously, intraveously, or intramuscularly.

9. The method of claim 1 wherein the pharmaceutically acceptable salt is methanesulfonate salt.

* * * * *

UNITED STATES PATENT AND TRADEMARK OFFICE
CERTIFICATE OF CORRECTION

PATENT NO. : 6,703,389 B2
DATED : March 9, 2004
INVENTOR(S) : Erik H.F. Wong et al.

It is certified that error appears in the above-identified patent and that said Letters Patent is hereby corrected as shown below:

Column 20,
Line 2, please delete "parentarally" and insert -- parenterally -- in its place.

Signed and Sealed this

Fourteenth Day of December, 2004

JON W. DUDAS
*Director of the United States Patent and Trademark Office*